US00PP28049P3

(12) United States Plant Patent
Wood

(10) Patent No.: US PP28,049 P3
(45) Date of Patent: May 23, 2017

(54) ***GREVILLEA* HYBRID PLANT NAMED 'RR01'**

(50) Latin Name: ***Grevillea* hybrid**
Varietal Denomination: RR01

(71) Applicant: Michael Wood, Bega (AU)

(72) Inventor: Michael Wood, Bega (AU)

( * ) Notice: Subject to any disclaimer, the term of this patent is extended or adjusted under 35 U.S.C. 154(b) by 0 days.

(21) Appl. No.: 14/999,170

(22) Filed: Apr. 5, 2016

(65) Prior Publication Data

US 2016/0309634 P1 Oct. 20, 2016

(30) Foreign Application Priority Data

Apr. 14, 2015 (AU) ..... PBR 2015/075

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Samuel R. McCoy, Jr.

(57) ABSTRACT

A new and distinct *Grevillea* hybrid cultivar named 'RR01' which is characterized by a very prostrate growth habit with a vigorous growth rate, dark green pinnatisect foliage with red immature branches, racemose inflorescence typical of the species with approximately 30 to 50 florets, and the stability of these characteristics from generation to generation.

1 Drawing Sheet

Latin name of the genus and species: The Latin name of the genus and species of the novel variety disclosed herein is *Grevillea* hybrid.

Variety denomination: The inventive variety of *Grevillea* hybrid disclosed herein has been given the variety denomination 'RR01'.

CROSS REFERENCE TO RELATED APPLICATIONS

This application claims priority to the Australian Plant Breeder's Rights application number 2015/075, filed on Apr. 14 2015, which is herein incorporated by reference.

BACKGROUND OF THE INVENTION

Parentage: In July 2004, a unique *Grevillea* seedling was discovered by the inventor at his commercial nursery in Kalaru, New South Wales, Australia. The seedling exhibited a very vigorous growth rate, a prostrate growth habit, and pinnatisect leaves. The seedling was presumed to be an interspecific cross of *Grevillea* hybrid 'Poorinda Royal Mantle' (unpatented) and *Grevillea* hybrid 'Bronze Rambler' (unpatented), because the two varieties were being grown in close proximity and the new seedling exhibited characteristics of each variety. The new seedling was isolated and grown to a mature size to confirm the distinctness and stability of the characteristics initially observed. After further evaluation and confirmation of the desirable traits, the claimed plant was selected for commercialization and given the breeder denomination, 'RR01'.

Asexual Reproduction: 'RR01' was first asexually reproduced by way of softwood stem cuttings in 2005 at the inventor's nursery in Kalaru, New South Wales, Australia. It was found to grow uniform and reproduce in a stable manner and 10 successive cycles of vegetative propagation have proven to be true to type also.

SUMMARY OF THE INVENTION

The following characteristics have been repeatedly observed and represent the distinguishing characteristics of the new *Grevillea* cultivar 'RR01'. These traits, in combination, distinguish 'RR01' as a new and distinct cultivar.

1. *Grevillea* hybrid 'RR01' exhibits a very prostrate growth habit; and
2. *Grevillea* hybrid 'RR01' exhibits a very vigorous rate of growth; and
3. *Grevillea* hybrid 'RR01' exhibits dark green foliage with red immature branches; and
4. *Grevillea* hybrid 'RR01' exhibits broad, pinnatisect foliage; and
5. *Grevillea* hybrid 'RR01' exhibits a racemose inflorescence, typical to that of the genus, with 30 to 50 red florets.

BRIEF DESCRIPTION OF THE FIGURE

The figure illustrates, as nearly true as it is reasonably possible to make the same in color photographs of this type, an exemplary 2 year old 'RR01' plant grown outdoors in Clarendon, New South Wales, Australia.

BOTANICAL DESCRIPTION OF THE PLANT

The following is a detailed botanical description of a new and distinct variety of a *Grevillea* hybrid ornamental plant known as 'RR01'. Plant observations were made on plants grown in Clarendon, New South Wales, Australia. Unless indicated otherwise, the descriptions disclosed herein are based upon observations made from 2 year-old mature 'RR01' plants grown outdoors in full sun. Plants were not fertilized and were periodically watered with overhead irrigation, as needed. No pest and disease measures were taken. Observation data was recorded in the March of 2016.

Those skilled in the art will appreciate that certain characteristics will vary with older or, conversely, younger plants. 'RR01' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2003 edition except where common terms of color are used.

A botanical description of 'RR01' and comparisons with the presumed parents are provided below.

General plant description:

*Plant habit.*—Prostrate; flat and spreading.

*Height.*—Approximately 200 mm.

*Width.*—Approximately 200 cm.

*Hardiness.*—USDA Zone 9 to 11.

*Environmental tolerances.*—'RR01' has not yet been observed under all conditions but has shown to be heat tolerant, adapting well to temperatures of 103 degrees Fahrenheit without any noticeable damage. It has survived light to moderate frosts and temperatures down to 22 degrees Fahrenheit.

*Drought tolerance.*—'RR01' has not yet been observed under all conditions but it has shown good drought tolerance typical of the species once established.

*Pest and disease susceptibility or resistance.*—In common with the species.

*Propagation.*—Propagation is accomplished using softwood cuttings.

*Time to develop roots.*—4 to 5 weeks.

*Crop time.*—From 10 to 12 weeks are needed to produce a fully rooted cutting, depending on geographic location.

Root system:

*Description.*—Shallow system of proteoid roots, consisting of tight groupings of many small rootlets.

Stems:

*Branching habit.*—Single main stem which freely branches; numerous prostrate secondary branches.

*Stem strength.*—Strong.

*Dimensions.*—Main stem to 20 mm diameter, many laterals 3 to 5 mm in diameter.

*Cross-section.*—Round.

*Internode length.*—Approximately 35 mm.

*Color.*—Immature stems are closest to RHS 175B, and mature stems are greyed-brown 199A.

*Texture and pubescence.*—Smooth and corky; very finely pubescent with silky hairs.

Foliage:

*Arrangement.*—Alternate.

*Attachment.*—Petiolate.

*Shape.*—Both lanceolate and pinnatisect leaves are observed.

*Length.*—Approximately 95 mm for both pinnatisect and lanceolate leaves.

*Width.*—34 mm on pinnatisect leaves, and 24 mm on lanceolate leaves.

*Thickness.*—0.9 mm.

*Apex.*—Mucronate.

*Base.*—Cuneate.

*Margin.*—Entire (lanceolate leaves) to deeply lobed (pinnatisect leaves).

*Texture and pubescence, adaxial surface.*—Finely textured and glabrous.

*Texture and pubescence, abaxial surface.*—Finely textured, with dense fine hairs.

*Color.*—Juvenile foliage, adaxial surface — RHS 144A. Juvenile foliage, abaxial surface — RHS 192C. Mature foliage, adaxial surface — RHS 137A. Mature foliage, abaxial surface — RHS 192A.

*Venation.*—Pattern — Reticulate. Vein color, adaxial surface — 193A Vein color, abaxial surface — 193A.

*Petiole.*—Dimensions — 10 mm long and 1.2 mm in diameter. Color — 175A. Texture and pubescence — Smooth and finely pubescent. Stipules — None.

Inflorescence:

*Type.*—Terminal and axillary racemes with clusters of approximately 30 to 50 flowers.

*Natural flowering season.*—Spring to summer in the southern hemisphere.

*Dimensions.*—Dimensions vary but a mature terminal raceme is up to 60 mm in length, from the base of the peduncle to the stigma of the terminal-most flower, and approximately 50 mm wide, from style to style of the most outstretched lateral flowers.

*Quantity.*—Moderately floriferous.

*Peduncle.*—Dimensions — 25 mm long and 1.3 mm wide. Attitude — Lateral to stem approximately; approximately 30 degrees from horizontal. Color — RHS 175B. Texture and pubescence — Smooth and corky; very finely pubescent with silky hairs. Strength — Strong.

Bud:

*Dimensions.*—9 mm long and 3 mm in diameter.

*Shape.*—Narrowly oblong and clubbed at the distal end.

*Color.*—RHS 181A.

*Pubescence.*—Finely pubescent.

Flower:

*Pedicels.*—Dimensions — 2.5 to 3 mm long and 1.0 mm wide. Color — RHS 175B. Texture and pubescence — Smooth and corky; very finely pubescent. Strength — Strong.

*Perianth.*—

*General description.*—Small, pedicellate floret with a closed perianth which creates a floral tube made up of two dorsal and two ventral tepals, which terminate at their apex and form a ball-like "tepal limb" which house the anthers.

*Quantity of flowers.*—30 to 50 flowers per inflorescence.

*Sequence and rate of opening.*—Racemose; sequential proximal to distal, moderate around 5 days from first to last on each inflorescence.

*Persistence.*—Not persistent.

*Fragrance.*—Not fragrant.

*Aspect.*—Erect.

*Tepals.*—Quantity — 4 fused tepals. Arrangement — Fused into a tube. Dimensions — Perianth tube width is approximately 3 to 4 mm, with an average length of 10 mm. Texture, pubescence and luster — Smooth, pubescent with fine, silky hairs, and matte luster. Color when opening — RHS 52B. Color when fully opened — RHS 52B. Petal color fading to — Not fading.

Reproductive organs:

*Stamens.*—Quantity — Four. Attachment — Adnate to the perianth tube. Anthers — Shape — Irregularly triangular. Diameter — 1 mm. Color — RHS 12D. Pollen — Low to medium. Pollen Color — RHS 155C.

*Pistils.*—Quantity — One. Dimensions — Approximately 27 mm long and 1 mm wide. Stigma — Shape — Club-like. Color — RHS 145A. Style — Dimensions — 25 mm long and 1 mm wide. Color — RHS 52B. Ovary — Position — Superior. Dimensions — 15 mm long and 10 mm wide. Texture and pubescence — Smooth and finely pubescent.

Seed:

*Quantity.*—One.

*Shape.*—Ovoid with a thin papery wing that is approximately 1 mm wide.

*Color.*—Brown.

*Dimensions.*—10 mm long and 5 mm in diameter.

COMPARISONS WITH THE PRESUMED PARENTS AND CLOSEST KNOWN VARIETY

'RR01' may be distinguished from the presumed parent *Grevillea* hybrid 'Poorinda Royal Mantle' (unpatented), which is also the closest know commercial comparator, by the following combination of characteristics:

1. The mature foliage of 'RR01' is dark green, whereas the foliage of 'Poorinda Royal Mantle' is green and tinged greyed-orange.
2. The mature foliage of 'RR01' is typically pinnatisect, whereas the mature foliage of 'Poorinda Royal Mantle' is typically lanceolate to irregularly lobed.
3. Plants of 'RR01' grow to approximately 20 cm tall, whereas plants of 'Poorinda Royal Mantle' grow to approximately 25 cm tall.

'RR01' may be distinguished from the presumed parent *Grevillea* hybrid 'Bronze Rambler' (unpatented) by the following combination of characteristics:

1. Plants of 'RR01' are very prostrate, whereas plants of 'Bronze Rambler' exhibit a semi-prostrate to low, mounded habit.
2. While the mature foliage of both 'RR01' and 'Bronze Rambler' is pinnatisect, the individual lobes of 'RR01' are broader than those of 'Bronze Rambler'.

That which is claimed is:

1. A new and distinct variety of *Grevillea* hybrid plant named 'RR01', substantially as described and illustrated herein.

* * * * *

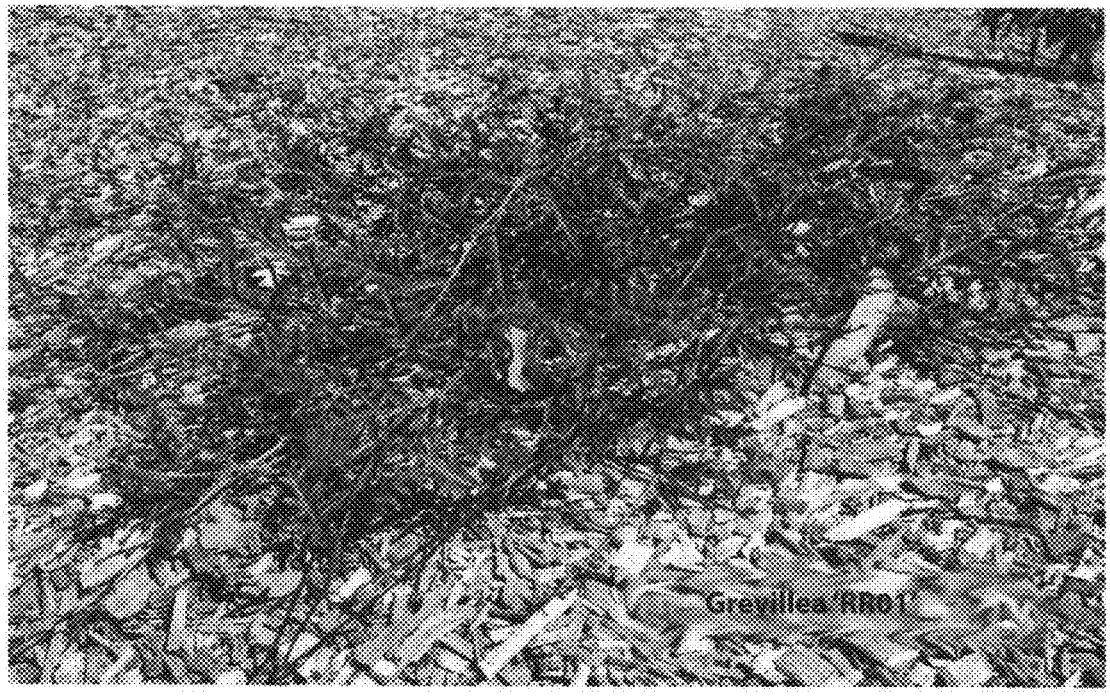
Grevillea RR01